United States Patent [19]

Brown

[11] Patent Number: 4,741,736
[45] Date of Patent: May 3, 1988

[54] PROGRAMMABLE INFUSION PUMP

[75] Inventor: Eric W. Brown, Redondo Beach, Calif.

[73] Assignee: I-Flow Corporation, Irvine, Calif.

[21] Appl. No.: 940,044

[22] Filed: Dec. 10, 1986

[51] Int. Cl.⁴ .............................................. A61M 5/20
[52] U.S. Cl. .................................... 604/134; 604/67; 604/131
[58] Field of Search .................. 604/7, 67, 65, 153, 604/131, 134, 135, 151, 154

[56] References Cited

U.S. PATENT DOCUMENTS

| | | |
|---|---|---|
| 2,848,141 | 8/1958 | Intagliata . |
| 3,029,983 | 4/1962 | Wagenhals . |
| 3,151,616 | 10/1964 | Selfon . |
| 3,647,117 | 3/1972 | Hargest . |
| 3,670,926 | 6/1972 | Hill . |
| 3,884,228 | 5/1975 | Hahn . |
| 3,895,631 | 7/1975 | Buckles et al. . |
| 4,044,764 | 8/1977 | Szabo et al. . |
| 4,077,405 | 3/1978 | Haerten et al. . |
| 4,111,198 | 9/1978 | Marx et al. . |
| 4,140,117 | 2/1979 | Buckles et al. . |
| 4,207,871 | 6/1980 | Jenkins . |
| 4,265,241 | 5/1981 | Portner . |
| 4,313,439 | 2/1982 | Babb . |
| 4,340,153 | 7/1982 | Spivey . |
| 4,410,322 | 10/1983 | Archibald . |
| 4,417,889 | 11/1983 | Choi . |
| 4,435,173 | 3/1984 | Siposs et al. . |
| 4,447,224 | 5/1984 | DeCant et al. . |
| 4,498,843 | 2/1985 | Schneider et al. . |
| 4,507,112 | 3/1985 | Hill et al. . |
| 4,525,164 | 1/1985 | Loeb et al. . |
| 4,563,175 | 1/1986 | LaFond . |

FOREIGN PATENT DOCUMENTS 2855713 12/1978 Fed. Rep. of Germany .

Primary Examiner—C. Fred Rosenbaum
Assistant Examiner—Gene B. Kartchner
Attorney, Agent, or Firm—Robert M. Asher

[57] ABSTRACT

A cartridge, a control system and an infusion pump provide an infusion system. The cartridge contains one or more flexible compartments and pressure roller for squeezing fluid from the compartments. When there is a plurality of fluid compartments in the cartridge, a multilumen connector is provided on the cartridge so that it may be connected to a single multilumen catheter. The control system monitors the volume of fluid which is expelled from the fluid filled compartments during the infusion process. Any errors in rate or volume are continually fed back to the infusion pump. Errors exceeding allowable limits cause adjustment to correct for the error in volume so that over a long duration information process desired dosage is infused at an accurately maintained infusion rate. The infusion pump is provided with a constant force spring connected to a sliding member. The sliding member is pulled against the pressure roller of the cartridge to cause a fairly constant flow of fluid from the cartridge during the infusion. The pump is also provided with an optical sensing sytem for determining the position of the pressure roller and thereby the volume of fluid which is being infused. The cartridge has a position indicating strip for use with the optical sensing system in order to provide the position information.

37 Claims, 4 Drawing Sheets

PROGRAMMABLE INFUSION PUMP

BACKGROUND OF THE INVENTION

This invention relates to a method and apparatus for infusing fluids accurately in terms of dosages or infusion rates. In particular it relates to a programmable infusion pump that receives a multiple fluid cartridge.

Infusion pumps are used to administer a variety of drug therapies to patients. Examples of two such diverse applications are the administration of chemotherapy drugs to cancer patients and the administration of heart-rate control drugs to cardiac patients.

The patient receiving drugs which are used to control his heart rate needs to have the fluid delivered at an extremely constant rate because the rate of his heartbeat is proportional (or inversely proportional, as the case may be) to the amount of drug delivered. If the rate of infusion were to decrease or increase significantly, the heart would pump more slowly or more quickly than desired. It is important for the infusion pump administering these drugs to return as quickly as possible to the proper infusion rate.

The volume of a heart rate control drug which was overinfused or underinfused does not have to be corrected for. If, for example, a volumetric correction was made to infuse an additional bolus of drug because the pump had slowed down, the patient might find his heart beating overly fast for a period of time. This would be highly undesirable and might even be dangerous for the patient. This type of therapy is referred to herein as a rate-dependent therapy, and many other examples of such therapies exist.

Another type of therapy which requires an infusion pump is the administration of chemotherapy drugs to cancer patients. A recent trend in the administration of chemotherapy is to provide for a slow, continuous infusion in place of the tradition bolus injection of a cytotoxin. It has been found by many cancer researchers and oncologists that the severe side-effects of chemotherapy, such as nausea, vomiting, diarrhea, anorexia, and lassitude, may be reduced in a significant number of patients if the drugs are administered in lower dosages over a prolonged period of time.

As an example relating to infusion pumps, the dosage of certain cytotoxins which may be administered is determined by approximating the surface area of the skin of the patient. The number of milligrams of drug to be administered for each square meter of skin per day for a given therapy is then computed. This amount of drug may then be administered by the traditional bolus injection in a few seconds or by the more advantageous continuous infusion method over a period of hours or even days.

When the more advantageous continuous infusion method is used, it becomes apparent that the infusion device must endeavor to administer the required volume (i.e., number of prescribed milligrams) of drug for a period of days. This type of therapy is referred to herein as a dosage-dependent therapy or volume-dependent therapy.

For an infusion device to perform this dosage-dependent therapy accurately, it must maintain a fairly constant infusion rate and determine if any undesired fluctuations in rate occurred. There must be a correction for the amount of drug which was underinfused or overinfused during a period of fluctuation.

For example, if the device were infusing the cytotoxins to the cancer patient too slowly for a period of time, it must determine how many milligrams of drug were not infused and it must then correct for the deficiency by infusing an additional amount of drug for a period of time. After the correction has been made, the pump must endeavor to return to the desired rate so that the prescribed amount of the remaining drug is administered to the patient in the required time period.

The small volumetric errors caused by the mechanism of conventional infusion pumps, as illustrated in the cardiac patient example, are not advantageous in the drug therapy of a cancer patient because they can build up to substantial cumulative errors over a long period of time. This is especially true when the pump is being used in an ambulatory patient who is not subject to continuous surveilance.

It is an object of the method of the present invention to provide physicians with the means for properly administering dosage-dependent therapies.

In recent times it has become increasingly desirable to provide an infusion pump which is compact and lightweight so that it may be used by an ambulatory patient. Ambulatory infusion pumps reduce the need for excess use of hospital facilities and resources. In order to provide a lightweight pump it is highly desirable that a pump require a minimal amount of electric power since power sources, such as batteries, can contribute substantially to the weight of a pump.

It is another object of this invention to provide for a compact, lightweight infusion pump which may be used by ambulatory patients.

There are also an increasing number of applications for which there is a need for a pump which can intravenously administer a plurality of drugs solutions. One such application is the use of chemotherapy to treat such diseases as cancer. Many of the drugs used in chemotherapy and other therapies cannot be mixed together prior to an infusion. Some of these drugs react to neutralize one another. Other drugs react to form precipitates which may block the catheter tube or possibly cause an embolism in the patient.

It is often found that when different incompatible drug solutions are used on a single patient, they are administered by using a separate catheter tube for each drug. A separate infusion pump would then be used on each individual catheter tube line and the tube would deliver the fluid solution into the patient through its respective intravascular access needle. Since a patient must pay for each catheter set and must rent a pump for use with each catheter tube, it becomes costly to use multiple catheter tubes and pumps. There is some danger of infection any time an opening is made in a patient's skin for a catheter. The likelihood of infection increases as more openings are made to accommodate multiple lines.

It is therefore yet another object of this invention to provide a single pump, with a single vascular-entry catheter set, that can deliver a multiplicity of drug solutions without mixing any of them prior to infusion. It is still yet another object of this invention to provide an ambulatory infusion pump which can administer several different drug solutions without mixing any of the fluids together.

SUMMARY OF THE INVENTION

The infusion pump of the present invention is achieved by using a unique multiple fluid cartridge assembly. The cartridge houses a plurality of flexible compartments and a pressure roller which rolls over the compartments to squeeze fluid out through their outlet opening. A plurality of access tubes connect to the openings in the flexible compartments and a multiple port connector is provided so that a single multilumen catheter can be easily connected to the cartridge for use in the infusion process. The cartridge is advantageously constructed with a resilient base to better insure that fluid does not leak behind the roller when it presses against the fluid compartments.

The cartridge may be advantageously provided with position markings along the length of the housing. These markings can be used to monitor the position of the pressure roller during the infusion process. The pump of the present invention includes an optical sensor which can read from the position markings to give a determination of where the pressure roller is. The pump is provided with a microprocessor type controller which can calculate the rate at which fluid is being delivered from the pump as a function of the time it has taken the roller to travel a measured distance. The pump of the present invention is advantageously powered by a constant force spring. Thus, the power is provided mechanically when the cartridge is inserted into the pump. There is no need for electrical power to push fluid out of the pump. A motor is provided however which controls a flow restriction valve. If the microprocessor determines that the pump is not operating at the predetermined rate, the position of the valve is changed to increase or decrease the rate of infusion. It requires very little power to occasionally operate the valve during an infusion process.

The cartridge pump of the present invention advantageously employs a novel method for maintaining highly accurate infusion rates. The optical emitter and sensor monitor the position of the pressure roller by reading the position markings. The location is fed into the programmable controller. The distance travelled from the beginning of the infusion is used in determining the total volume of the fluid which has been infused. The amount of fluid which is delivered per distance travelled by the roller is already known by the controller. The controller also determines the current rate of infusion by taking the volume of fluid infused in a predetermined distance and dividing it by the time it took the pressure roller to progress that distance. Thus the current rate and the total volume can be compared to the predetermined rate and volume. The comparison can be accomplished repetitively throughout the infusion process. By making a correction whenever the rate error or volume error exceeds a threshold value an accurate infusion rate can be maintained throughout the infusion process. This method is thus highly advantageous for use in dosage dependent and rate dependent therapies.

Other objects and advantages of the present invention will become apparent during the following description of the presently preferred embodiment of the invention taken in conjunction with the drawings.

DETAILED DESCRIPTION OF THE PREFERRED EMBODIMENTS

Figure 1:
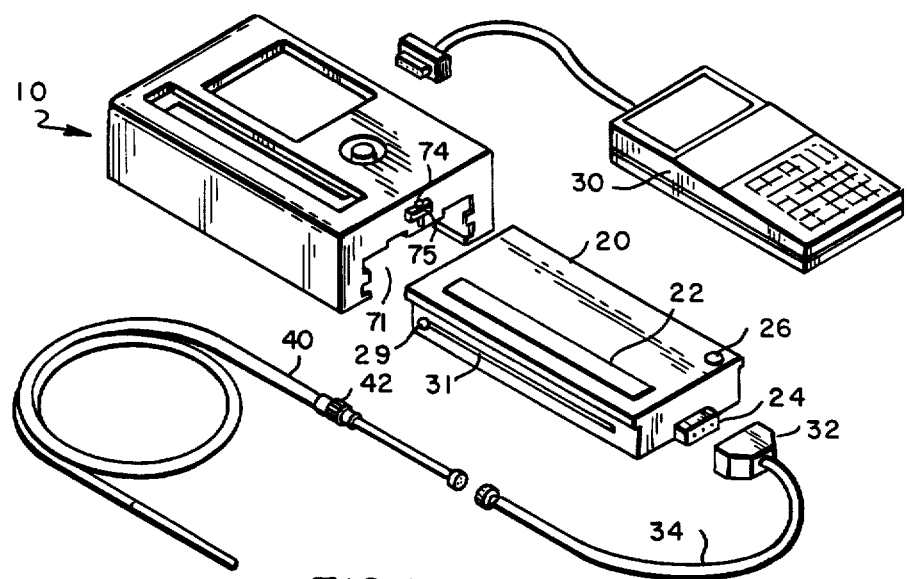
FIG. 1 illustrates a multilumen infusion system using the pump and cartridge of the present invention.

Referring now to FIG. 1, the various pieces of a multilumen infusion system using the present invention are shown. The present invention includes a constant pressure infusion pump 10 which receives a multiple drug cartridge 20. The pump 10 of the preferred embodiment is powered by a constant force spring. A position indicating strip 22 is located on the multiple drug cartridge 20 for use by the pump 10 in monitoring the rate of infusion. The total volume of drug to be infused and the desired length of time for the infusion is programmed into the pump by a detachable programming unit 30.

The multiple drug cartridge 20 includes a multiple port connector 24. The multiple port connector 24 provides an outlet for each of the fluids being pumped from the cartridge 20. The multiple port connector 24 is adapted for connection to a connector 32 on a multilumen catheter 34. In the embodiment shown, the multiple port connector 24 and connector 32 snap-fit together. Of course, other multilumen connectors could be substituted for the snap-fit connectors. For example, at the other end of multilumen catheter 34 is a multilumen catheter connector with a threaded locking ring. Such a multilumen locking connector is disclosed in U.S. Pat. No. 4,581,012, issued Apr. 8, 1986, the disclosure of which is incorporated by reference herein. The multilumen locking connector is used to connect multilumen catheter 34 to an implantable multilumen catheter 40. The implantable multilumen catheter includes a tissue cuff 42 for forming a seal with the skin of a patient.

The multilumen infusion system of FIG. 1 provides for a simple and controlled infusion of a plurality of fluid solutions into a patient. Although the invention as described herein derives significant advantages from providing a plurality of fluid solutions through a multiple lumen catheter set, the infusion pump and cartridge of the present invention may also be made for use with a single fluid cartridge and conventional single lumen catheter.

Figure 2:
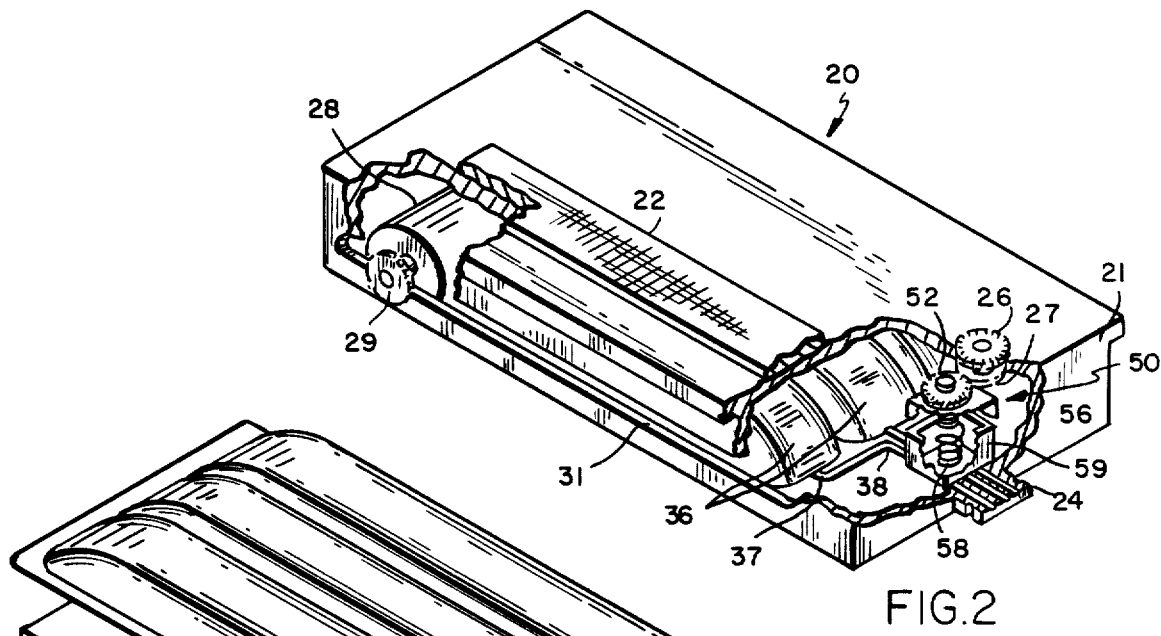
FIG. 2 is a perspective view with portions cut away of the cartridge of the present invention.
Figure 3:
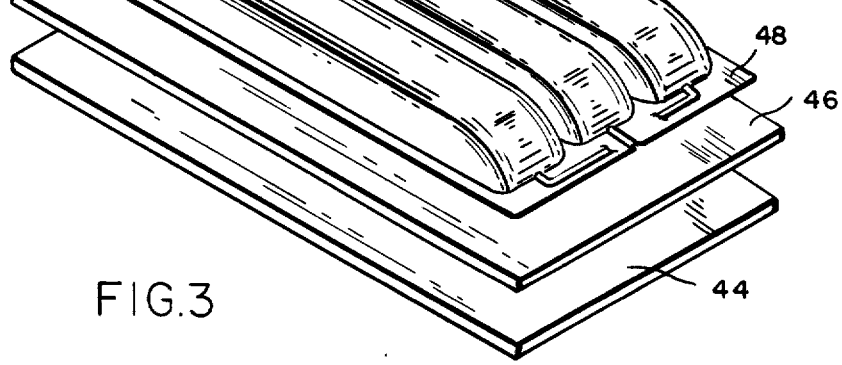
FIG. 3 is an exploded view of the base portion of the cartridge housing of FIG. 2.

Referring now to FIGS. 2 and 3, the multiple drug cartridge 20 of the present invention is shown in greater detail. The cartridge 20 is contained by a housing 21 which carries a plurality of flexible fluid containing compartments 36. Each compartment 36 has an outlet 37 connected to an access tube 38. A pressure roller 28 is provided inside the cartridge for rolling over the flexible compartments 36 in order to squeeze fluid out through the access tubes 38. The access tubes 38 extend into the multiple port connector 24. The pressure roller 28 includes a knob 29 on either side which extends from the cartridge for engaging a drive mechanism in the pump 10. The drive mechanism of the present invention is a sliding member pulled by a constant force spring. In accordance with the presently preferred embodiment, the knobs 29 extend from both ends of the pressure roller and ride within a pair of slots or tracks 31. It may also be possible to provide an open faced cartridge for use in a pump which already contains a pressure roller. However, the presently preferred arrangement is to include the roller 28 within the cartridge.

In order to control the rate of infusion of fluids from the cartridge 20, a flow restrictor valve 50 is provided for interaction with the access tubes 38. The valve 50 is controlled by an external gear 26 which is engageable with a mating gear inside the pump 10. Turning the gear 26 will change the pressure exerted upon the access tubes 38 by the valve 50. The more pressure which is applied by the valve 50 to the access tubes 38 the more restricted the flow of fluids therethrough. The valve 50 can be wound entirely down against the access tubes to completely close off fluid flow when desired.

The bottom of the cartridge housing 21 is a solid base member 44. Overlaying the solid base member 44 is a resilient layer 46. The resilient layer 46 is compressible by the pressure roller 28. Thus, as the pressure roller 28 is moved along the slots 31 through the cartridge a tight seal is formed between the roller 28 and the resilient layer 46 to prevent fluid from escaping behind the roller within a flexible compartment 36. All fluid is forced out through the access tubes 38. It is the resiliency of the layer 36 which causes it to push up against the roller 28 as the roller is held within the slots 31 down against the layer 46 thus forming the tight seal. The flexible compartments 36 are formed on the resilient layer 46 by a plastic molded layer 48. Layer 48 is molded in the shape of a plurality of compartments with an access tube 38 leading from each compartment. It would of course be possible to practice the invention using flexible bags to contain fluids instead of the multilayer construction described herein. In the presently preferred embodiment, both layer 46 and layer 48 are made of silicone, such as Dow Corning Silastic.

The relative infusion rate of the fluids in the compartments is determined by the geometry of the compartment. When the compartments are all the same size then the fluids in each are infused at the same rate. It is preferable that each compartment has the same length but varies in width or height to provide a different volume compartment. With all compartments the same length those with a larger width and/or height will have a larger volume. Thus when the roller moves a certain distance along the lengths of the compartments those with a larger width and/or height will have expelled a greater volume of fluid. Hence, the infusion rate is faster for the larger volume compartment. The infusion rate is proportional to the relative volume of the compartment.

In accordance with an alternative embodiment of the invention, the fluid containing compartments may be syringe barrels each with a piston for pushing fluid out of the syringe barrel. The pressure roller may be replaced by any slidable member attached to the constant force spring. The slidable member is pulled by the constant force spring against the syringe pistons to push fluid out of the syringe barrels.

Figure 4A:
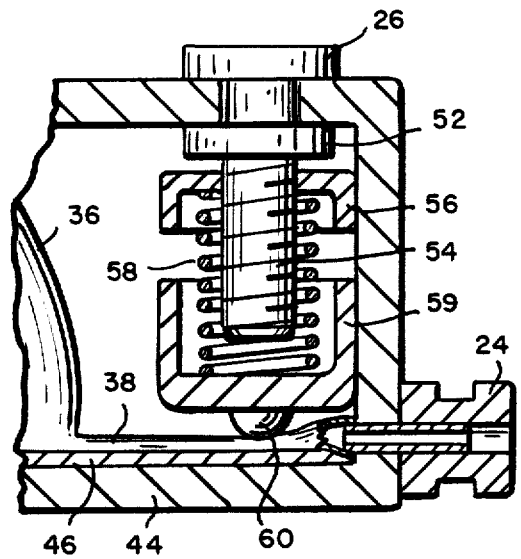
FIG. 4A is a cross-sectional view of the flow restrictor valve of FIG. 2 in an open position.
Figure 4B:
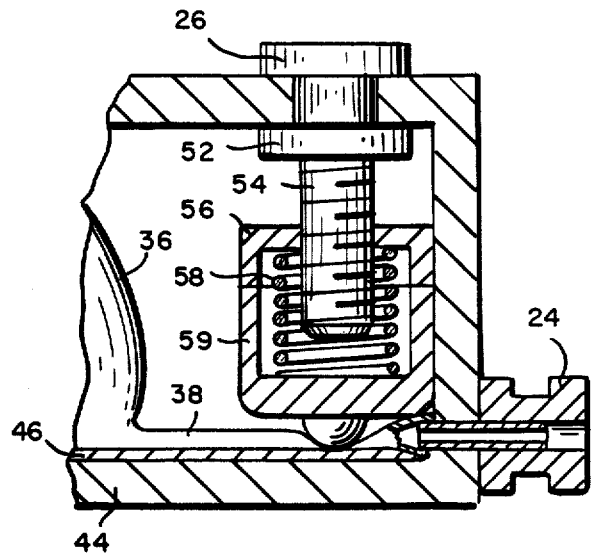
FIG. 4B is a cross-sectional view of the flow restrictor valve of FIG. 2 in the fully closed position.

The valve 50 of the present invention shall now be described in greater detail. The external gear 26 is directly connected to an internal gear 27. The internal gear 27 meshes with a second internal gear 52. Referring now to FIGS. 4A and 4B the second internal gear 52 is connected to a threaded cylindrical member 54. The threaded cylindrical member 54 engages a threaded hole within a non-rotating valve housing member 56. As shown in FIG. 2, the non-rotating member 56 is approximately square shaped and is prevented from rotating by the wall of the housing 21. The non-rotating member 56 acts to push against a coil spring 58. The spring 58 is held between the non-rotating housing member 56 and a lower housing member 59. At the bottom of the lower housing member 59 there is a compression member 60. As the threaded cylindrical member 54 is turned to force the non-rotatable housing member 56 against the coil spring 58 pressure is exerted downwards against the lower housing member 59 and the compression member 60. Thus the compression member 60 pushes against the access tubes 38 to restrict the flow of fluid therethrough. The compression member 60 can be pushed tight enough against the resilient member 46 so that the access tubes 38 are squeezed shut therebetween.

As shown in FIG. 4B, a positive mechanical seal can be achieved by further rotating the threaded cylindrical member 54, until there is direct contact between the non-rotating housing 56 and the lower housing member 59. This is desirable for situations that require a guaranteed seal, such as when the cartridge is prefilled at a pharmacy and transported to the physician. The threaded cylindrical member 54 may be turned in the opposite direction to relieve the pressure between the compression member 60 and the resilient base 46 so that fluid may flow through the access tubes 38. Thus, the rate of fluid flow through the access tubes 38 can be controlled by merely turning the external access gear 26 to give a variable degree of flow restriction to the fluids which are subjected to a constant force by the pressure roller 28 within the pump 10. It is also possible to use other types of flow restriction valves, such as needle valves.

The position indicating strip 22 is provided so that the location of the pressure roller 28 relative to the fluid compartments 36 can be detected through an appropriate sensing system. The position indicating strip 22 is oriented lengthwise in the direction of movement of the pressure roller 28. The strip 22 can be simply a plurality of equally spaced lines for which a simple sensing mechanism in the pump 10 can determine relative position by counting the number of lines crossed by the pressure roller 28. It is preferable, however, to provide the position indicating strip with coded information indicating the absolute position of the roller. The strip may appear something like that shown in FIG. 5. Access to absolute position from coded information has the advantage of allowing for determination of the position of the roller despite occasional, vibration-induced backward movement of the roller which could be interpreted by a line counter as an additional forward movement. In order to provide highly accurate infusion rate and volume information, the coded patterns on the position indicating strip 22 may be placed very close to one another, such as 10 microns apart. Depending upon the resolution desired, other greater distances between the coded patterns may suffice. The strip 22 is preferably reflective to make it easier to optically sense position. Knowing the position of the roller, the volume of fluid which has been infused into a patient can be readily determined.

The volume of the fluid which has been infused may be determined by multiplying the cross-sectional area of each flexible compartment 36 by the value assigned to each linear position of the roller. The flexible compartments 36 of the presently preferred embodiment have tapers near the starting and ending positions of the roller. These tapers, and the corresponding changes in cross-sectional area, are known functions of the shape of the mold that is used to manufacture the molded layer 48. This geometric information is stored in the microprocessor used to compute the infusion rate.

Figure 6:
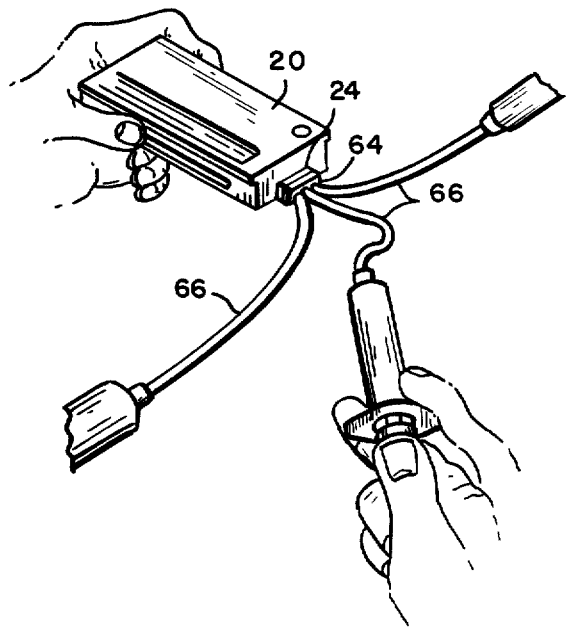
FIG. 6 is an illustration of a cartridge of FIG. 2 in the process of being filled with fluid.

The operation of the cartridge shall be discussed with reference to FIG. 6. It is expected that cartridges would be generally supplied with their fluid containing compartments in an empty condition. A fill adapter 64 is used in the process of filling the compartments 36 with fluid. The fill adapter 64 has a connector which snaps onto the multiple port connector 24 and includes a plurality of single lumen tubing 66 through which fluid may be injected. The external gear 26 is turned to open the access tubes 38. For each fluid, a syringe is filled with enough drug and solution to fill each fluid containing compartment 36 to capacity. The syringes containing the fluids are attached to the open ends of the tubing 66. The syringes are squeezed to expel fluid through the fill adapter 64 and into the fluid containing compartments 36. After each of the compartments has been filled in this manner, the cartridge 20 is held vertically with the connector 24 on top. The roller 28 is gently shaken in order to displace any air bubbles in the fluid containing compartments. The syringe stems are withdrawn slightly to see if any air bubbles are present. If any air bubbles appear near the multiple port connector 24, which may advantageously be made of a clear plastic material such as polycarbonate, the respective syringe stem should be slowly withdrawn until the bubble is inside the syringe. The syringe is then held in an inverted position so that the fluid may be returned to the cartridge, but the air remains in the fill adapter. Each line is double checked for air bubbles and air bubbles are pulled out of the cartridge with the syringe stems wherever necessary. After it has been ascertained that there are no air bubbles remaining in the fluid compartments within the cartridge 20, the external valve gear 26 is turned to close off the access tubes 38 as shown in FIG. 4B. The use fill adapter 64 is removed and discarded. A fluid filled cartridge is now available for use in the pump.

Figure 7:
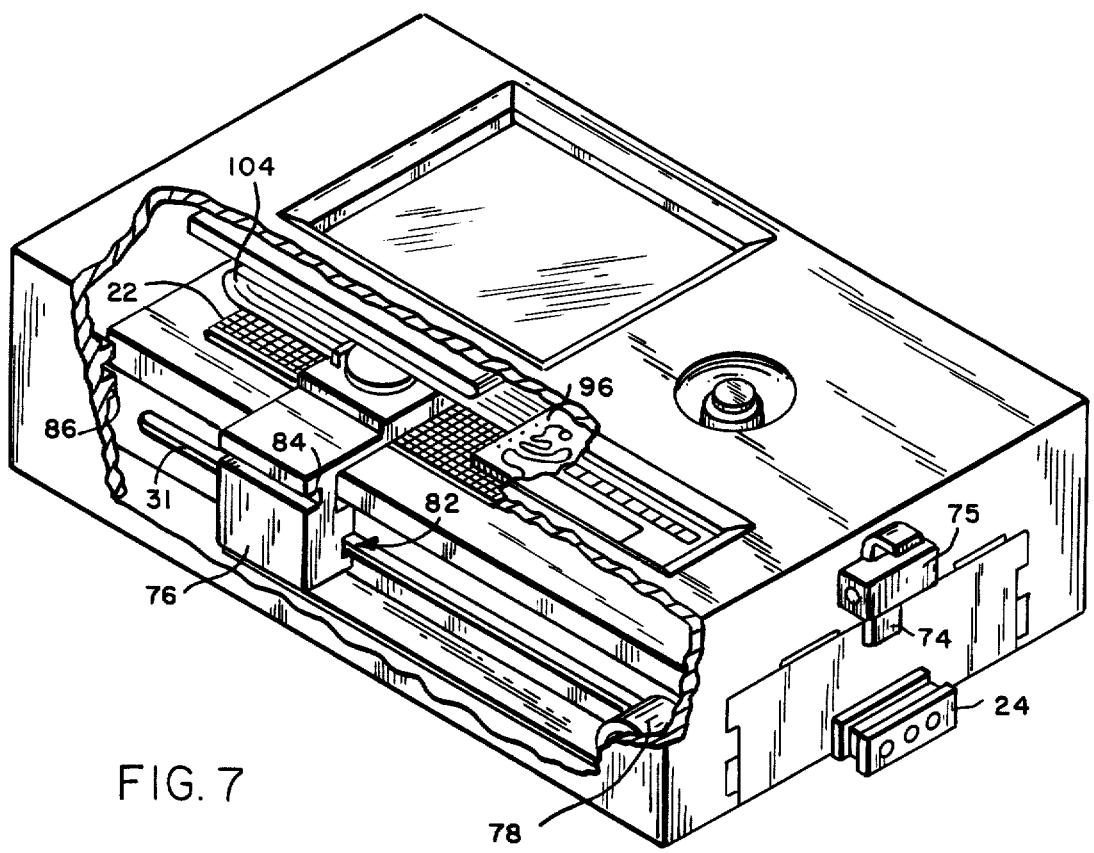
FIG. 7 is a perspective view partially cut away of the pump of the present invention.
Figure 8:
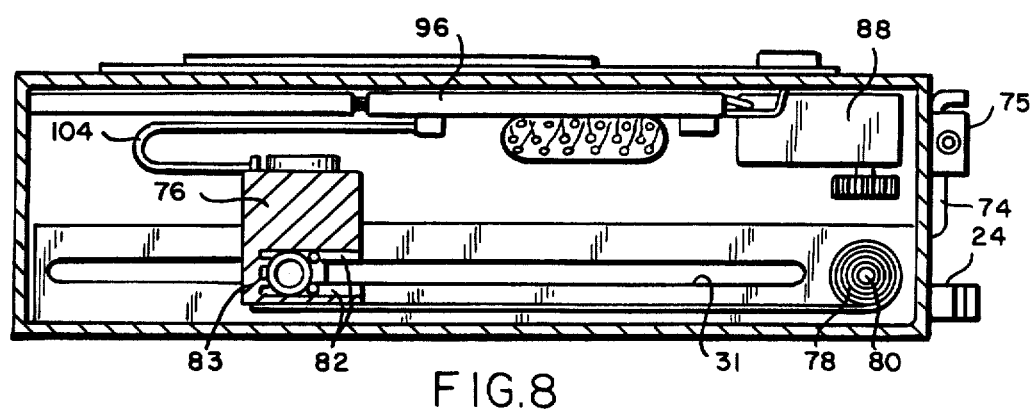
FIG. 8 is a side view in cross-section of the pump of FIG. 7.
Figure 9:
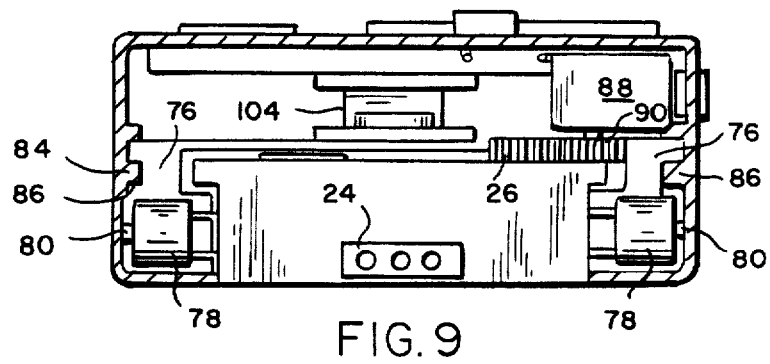
FIG. 9 is an end view in cross-section of the pump of FIG. 7.

Referring now to FIGS. 7, 8 and 9, the infusion pump 10 of the present invention is contained within a housing 11. The housing has an opening 71 through which the multiple fluid cartridge assembly is inserted. A locking device of any type may be used to hold the cartridge 20 inside the pump 10. A sliding peg 74 is shown in the drawings for use in locking the cartridge 20 within the pump 10. The peg 74 can slide back and forth within its mount 75, but the mount 75 maintains the peg captive so that it does not fall off of the device. On the inside, the pump 10 includes a sliding member 76 attached to a constant force spring 78. A constant force spring differs from a traditional tension or extension spring in that the output of the traditional spring increases (or decreases) linearly with position changes. The constant force spring provides a relatively stable output force regardless of position. Such springs are available from Stock Drive Products (New Hyde Park, N.Y.), model number SH08J28, as well as many other manufacturers. The constant force spring 78 is a metal coil. The metal coil constant force spring 78 is mounted on an idler spool 80. In accordance with the presently preferred embodiment there are two constant force springs, one on either side of the pump. The invention may just as well be made with one or any other number of constant force springs. The idler spools 80 are mounted to the pump housing 11. The spools 80 allow the coil spring 78 to rotate but prevent the springs from translational movement within the pump. The free end of the coil springs 78 are attached to the sliding member 76. The sliding member 76 has a channel 82 on its inner portion on either side of the incoming cartridge. The channels 82 do not go all the way through the sliding member 76. Rather, the channels 82 have a stop 83 which will butt against the knobs 29 of the pressure roller 28 on the cartridge 20. When a cartridge filled with fluid is inserted into the pump 10 the knob 29 on the pressure roller slide into the channel 82 of the sliding member until they hit the stops 83. Then further insertion of the cartridge pushes the sliding member to the rear of the pump unwinding the constant force spring 78. The sliding member 76 is pulled by the springs 78 against the pressure roller 28. The pressure roller pushes against the fluid filled compartments but is prevented from movement since the flow restrictor valve 50 is closed thereby preventing fluid from exiting from the compartments. The sliding member 76 includes a groove 84 on the outer side facing the wall of the pump housing. The grooves 84 are provided for riding within a track 86 on each side of the pump housing. The grooves 84 and track 86 maintain the sliding member in proper alignment on its movement through the pump. The pumping action begins when the flow restrictor valve 50 is opened from its closed position to allow fluid to flow out through the access tubes 38. Hence, the substantially constant force provided by the spring 78 pulls the sliding member 76 and consequently the pressure roller 28 against the fluid filled compartments to push fluid out of the pump.

It would be possible to have two sliding members, one on either side of the cartridge, however, a single sliding member connected by a bar over the top of the cartridge is preferred to provide a constant force across the fluid compartments and to provide a convenient location for the optical sensing system of the present invention.

In order to control the amount of pressure exerted by the flow restrictor valve 50 on the access tubes 38 the pump 10 is provided with a motor 88. The motor 88 is provided for turning a motor gear 90. The motor gear 90 engages the external cartridge gear 26 when the cartridge is fully inserted into the pump. An electrical button switch 92 can be provided on the outside of the pump to allow a user to turn the pump on or off. The pump has the indication "STOP" on the outside of the pump next to the button so that the patient knows that he can turn the pump off by depressing the button. When the pump is started by depressing button 92 the motor 88 will cause the gear 90 to turn. This causes gear 26 to likewise rotate thereby opening the valve 50 to allow fluid to begin flowing through the access tubes 38. In order to stop the pumping action, the motor will cause gear 90 to rotate in the opposite direction so as to cause valve 50 to close upon the access tubes. A battery 94 is provided for operating the motor 88. The battery 94 is also used for providing power to the microprocessor controller of the pump for operating the optical sensing system. Only a lightweight battery 94 is required because the motor is only needed from time to time after the proper flow rate has been established. A duty cycle for the motor of less than 2 seconds every 5 minutes is possible with the present invention. The electronics and optics also use only a small amount of electric power. It is highly advantageous that the power for pumping is provided by the mechanical spring 78. This advantageously avoids the need for the heavy power packs that are typically used with motor-driven pumps and avoids the fear that the power might run out during the infusion process.

A microprocessor based controller 96 is provided on a circuit broad. An electrical connector 98 is provided so that the detachable programming unit 30 can be used to set the infusion rate in the infusion pump 10. Other parameters of the infusion process may also be set by the programming unit 30. In addition, the programming rate may be a sequence of different rates which change from one to another over a long infusion process.

In accordance with the present invention, a unique control system is provided for regulating and maintaining an infusion rate delivered by an infusion pump to a patient. The control system includes the microprocessor controller 96 and the detachable programming unit 30. It will be understood that the detailed embodiment of the control unit 96 and the programming unit 30 itself form no part of the present invention, except to the extent that it provides one programmable control means available to those of ordinary skill in the art suitable for use in carrying out the steps of the present invention, the programming techniques for adapting a microprocessor controller to such steps being well known in the microprocessor and programmable control means art.

Figure 10:
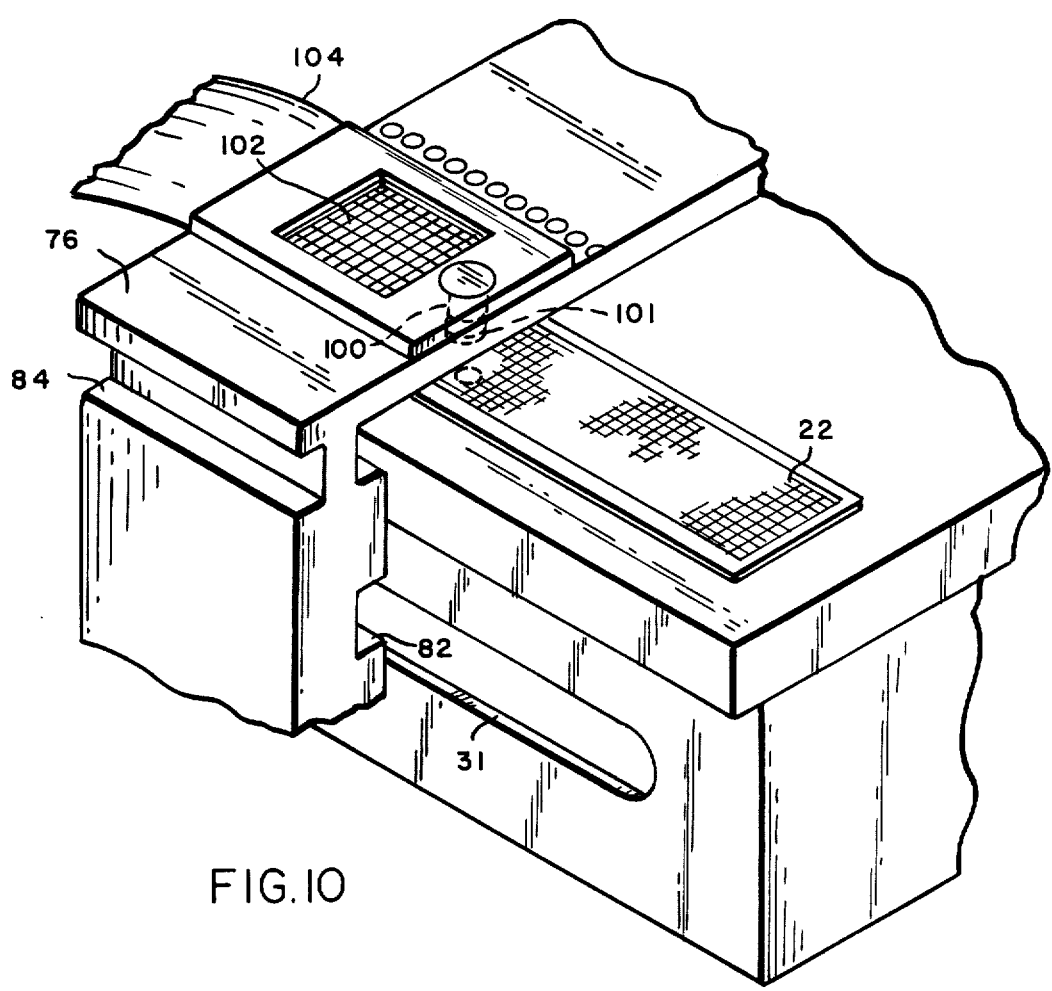
FIG. 10 provides an enlarged view of the optical sensing mechanism of the present invention.

Before turning to the steps of the infusion dosage control method of the present invention, the optical sensing system shown in FIG. 10 shall be described. An optical emitter 100 and optical detector 102 are carried on the sliding member 76 of the pump 10. Power is supplied to these devices through a flexible cable 104 connected to the control unit 96. Ultimately, of course, the power is supplied by the battery 94. The flexible cable 104 is also used to transmit information back and forth between the optical sensing system made up of the emitter 100 and detector 102 and the control unit 96. The emitter 100 may consist of a common LED or laser diode. A lens 101 may be provided to focus the light emitted by the emitter 100. The light illuminates a spot on the position indicating strip 22. Light reflected from the strip 22 is detected by a sensor which is used as the detector 102. For a simple strip 22 which contains a plurality of equally-spaced stripes, the detector 102 may be a phototransistor which is masked with a striped pattern similar to that on the position strip 22. The photo masking of the detector causes the detected spot to turn on and off as the sliding member 76 carries the emitter 100 and detector 102 across the strip 22. Commonly available NPN-Si Phototransistors such as the NTE3037 distributed by NTE Electronics, Inc. (Bloomfield, N.J.) may serve as such sensors. Equivalently, the emitter 100 could be masked with the striped pattern so that almost any light detector could easily identify moving the distance between two stripes. Alternative emitters and detectors may be readily selected by those of ordinary skill in the art.

Figure 5:
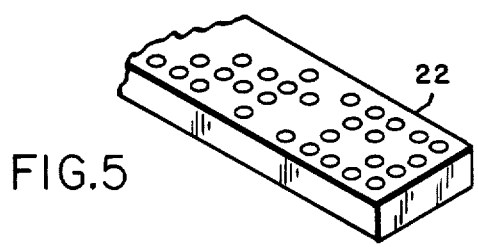
FIG. 5 is a magnified view of a portion of the position indicating strip of the present invention.

A more accurate strip 22 would have a pattern encoded onto the surface, as shown in FIG. 5, to allow the actual position of the roller to be determined. This encoded strip 22 would require an array sensor to serve as the detector 102. Such array sensors are manufactured by Micron Technology, Inc. (Boise, Idaho), Models IS32 OpticRam and IS6410 OpticRam. Other array sensors are also commercially available. These array sensors require the lens 101 which focuses the pattern on strip 22 onto the active detection area.

The information received by the detector 102 whether it be a coded pattern or a simple series of on-off pulses is transmitted over the cable 104 to the control unit 96 where it is interpreted by the microprocessor unit. The interpretation may be a simple matter of counting the number of lines which are passed by the sliding member 76 as it is moved or it may be a more complicated algorithm which reads the patterns inscribed on the position indicating strip 22 to determine the absolute position of the sliding member 76 and thus the location of the pressure roller 28.

As with any measurement instrument, it is necessary to calibrate the sensing mechanisms so that it can determine the amount of volume which is displaced by the pressure roller 28 as the sliding member 76 moves a certain distance. This calibration is achieved in the present embodiment of the invention, by storing position and volume profiles in the microprocessor. For any given cartridge, the relationship between the position of the sliding member 76 and the volume expelled from the compartment 36 is measured and stored in the programming unit 30. The position and volume profile for the cartridge type being used in the pump 10 is transferred into the control unit 96 of the pump 10 when a physician initializes the pump for determining its treatment regimen. The physician indicates the type of cartridge and the programming unit 30 transfers the appropriate profile to the control unit 96.

The method of the present invention for maintaining a controlled flow rate shall now be described. The unit dosage for the therapy is determined by the physician. The physician then calculates the number of milliliters, cubic centimeters or milligrams of drug or drugs which are to be administered over a given infusion time period. The volume of fluid is then determined which corresponds to the required dosage for each drug. A diluting solution may be used in the preparation of this volume, if desired by the physician. The volume of fluid is accurately measured in a measuring device, such as a syringe or graduated cylinder. Separate measuring devices are more advantageously used in the case of multiple drugs to prevent mixing. The fluids are loaded into the storage compartments of the cartridge in accordance with common safety procedures, such as air bubble removal discussed above. Then the detachable programming unit 30 is attached to the electrical connector on the pump. The programming unit will then issue prompts so that the doctor may input the identity of the cartridge and the desired regimen which the pump is to follow with respect to duration and infusion volume. Thus, the pump is informed of the volume of fluids contained in the compartments and the length of the time period over which the infusion is to take place. The pump is attached to the patient and started. The detachable programming unit 30 is then disconnected.

The programmable controller 96 in the pump receives position information from the position indicating strip 22 through the optical sensing system and the position data is interpreted. When the pressure roller reaches the end of the cartridge, the pump is stopped and the end of the cycle is indicated througn a visual or audible signal. The end of this infusion cycle may also be indicated by expiration of the infusion time period. The doctor can set a certain amount of time for the infusion to take place and at the end of that time the infusion process will be stopped and the flow restrictor valve will be closed.

The controller determines whether any change in position has occurred. If the pressure roller stops moving then the controller checks to see whether there is an occlusion. A test is performed to determine the presence of an occlusion by opening the valve slightly. If the roller still does not move, an occlusion is assumed. If it is determined that there has been an occlusion, the flow restrictor valve is closed to stop the pump and an alarm is set off visually or audibly. If no occlusion is determined to exist, then the controller returns to its program to adjust the valve for obtaining the appropriate flow rate. Other types of occlusion tests may be performed, such as measuring the pressure changes which occur in the fluid lines during the occlusion formation, but the presently preferred test is based upon an interpretation of pressure roller motion.

The controller determines the current flow rate at which the pump is operating by counting the time which has elapsed as the pressure roller moves a predetermined distance. The programmable controller has a built in time clock as is typical in the art for microprocessors. The programmable controller is provided with a program that allows it to correlate the linear position of the pressure roller to the volume of fluid which has been expelled through or from the infusion pump. As long as the microprocessor is informed of the proper position and volume profile for the particular construction of the cartridges and molded layers which will be used in the pump, the pump will function properly. When the detachable programming unit was attached to the infusion pump for setting the parameters of the infusion, the type of cartridge which was being inserted into the infusion pump was indicated to the pump. In this manner, the programmable controller of the pump will know which set of data to refer to in determining the correlation between the linear position of the pressure roller and the volume of fluid expelled from the flexible fluid filled compartments.

In accordance with the present invention, the calculated current flow rate is compared with the desired flow rate as was indicated to the control unit by the detachable programming unit 30. The error in the flow rate is determined and compared with a predeterminedd allowable error. If the allowable error has been exceeded, the controller will instruct the flow regulator to make a correction. The type of correction depends on whether a rate-dependent therapy or a dosage dependent therapy is being followed. For a rate dependent therapy, the flow restrictor valve is adjusted a small amount. The valve will continue to be adjusted until the rate error has been reduced to an acceptable level. For a dosage dependent therapy, the flow restrictor valve is adjusted opened or closed until any volume error has been substantially eliminated. The valve is then readjusted to more closely approximate the desired rate of infusion.

Further in accordance with the invention, for dosage dependent therapies in addition to checking the current flow rate for error, the controller compares the total volume which has been infused with the volume which should have been infused according to the programmed infusion regimen. If the volumetric error exceeds a predetermined limit, the flow restrictor valve is instructed to open or close until the volume error has been substantially eliminated. In the presently preferred embodiment, the maximum allowable volumetric error is 1.0 cubic centimeter of drug for the cartridge. If for example the cartridge has four 20 cc. chambers, the volumetric accuracy for each individual chamber is 0.25 cc. This corresponds to an accuracy of 1.25% for the total infusion process, regardless of the duration of the infusion. When a volumetric error has been corrected, the valve is readjusted so as to approximate the desired rate of infusion. When the infusion process progresses at the desired rate and is within the volumetric tolerances, the controller continually loops through its program checking the position being sensed, the change in position, the change in time and determining whether a rate or volumetric error exists. Most of the time no adjustment will be necessary and therefore very little electrical power is consumed. The process continues until the end of the infusion at which time the flow restrictor valve is closed.

Sample computer programs for implementing the control method of the present invention on an Apple II computer (manufactured by Apple Computer Co., Inc.) equipped with A6 T/D Timer Driver Board and A32 I/O Optically Isolated I/O Board (manufactured by Rogers Labs, Inc., Santa Ana, CA) are attached as Appendix A. A similar program may be written by one of ordinary skill in the art to operate the microprocessor selected for the controller of the device of the present invention.

In the presently preferred embodiment, an electronic control system with optical sensing capability monitors the infusion process volumetrically and any deviation from the desired rate is derived from the changes in volume that are sensed by the system. It is possible for one of ordinary skill in the art to devise other feedback sensors to accomplish the same volumetric measurement, such as by attaching strain gauges to a syringe barrel and measuring the position of the plunger.

In the presently preferred embodiment, a cartridge with a roller and one or more elastomeric chambers which can independently store a multiplicity of fluid solutions is used to hold the fluids as the roller position is being measured. Other chambers could be devised by one of ordinary skill which could be used to accomplish the same type of measurement, such as by mounting one or several syringes in a manifold and using the position of the plungers to measure the volume.

In the presently preferred embodiment, an electronic controller is used to determine if any substantial errors exist in the rate or volume of fluid delivered. Other controllers, such as a mechanical controller comprised of gears and cams, may be adapted to measure fluid delivery errors and correct for them.

Of course, it should be understood that various changes and modifications to the preferred embodiment detailed herein and to the method of administering a dosage-dependent therapy as described herein will be apparent to those skilled in the art. These changes described above and other changes can be made without departing from the spirit and scope of this invention and method, and without diminishing its attendant advantages. It is therefore intended that such changes and modifications be covered by the following claims.

APPENDIX A

```
]LOAD SLOWRATE2
]LIST

1  DET = 49316
2  POWR = 49312
3  RESET = 49314
4  LOCTIM = 49318
5  REM  INITIALIZE
10  POKE (POWR + 1),0
20  POKE (POWR),255
30  POKE (POWR + 1),4
40  POKE (POWR),255
50  POKE (RESET + 1),0
60  POKE (RESET),255
70  POKE (RESET + 1),4
80  POKE (RESET),253
90  POKE (DET + 1),0
100  POKE (DET),0
110  POKE (DET + 1),4
111  POKE (DET),255
120  POKE (LOCTIM + 1),0
130  POKE (LOCTIM),0
140  POKE (LOCTIM + 1),4
141  POKE (LOCTIME),255
142  RA = 0:HR = 0: REM  RA=AVG RATE CC/SEC   HR=AVR RATE CC/HR
143  DD = 0:DT = 0:DIST = 0:TIME = 0
144  LPTIM = 0:LTIM = 0:LDIST = 0
145  REM  DD=DELTA DIST  DT=DELTA TIME   LPTIM=LAST PULSE TIME  LTIM=TIMER LOOP COUNTER  LDIST=LAST DISTANCE
146  PBITS = 0:TBITS = 0:SEC = 0
147  DCNT = 0: REM  DETECTOR COUNT
148  QIN = 0:T1 = 0:T2 = 0:T3 = 0: P1 = 0:P2 = 0:P3 = 0
150  REM  END INITIALIZATION CYCLE
151  PRINT  CHR$ (4)"BLOAD RMPDATA"
152  PRINT  CHR$ (4)"BLOAD RMPDATB"
153  PRINT  CHR$ (4)"BRUN AMPRAMP"
154  CALL 36864:YMODE% = 0
155  POKE (POWR),0:F = 0:EU = 0
160  POKE (RESET),254: REM  RESETS BOTH COUNTERS
161  HOME : HTAB 9: PRINT "I-FLOW CORPORATION"
```

```
162  HTAB 9: PRINT "CONTROL VALVE
     DEMO"
163  PRINT "TIME="
164  PRINT "INCREMENTS TRAVELED="
165  PRINT "TIME BET' J LAST TWO
     PULSES="
166  PRINT "ACTUAL TIME OF LAST P
     ULSE="
167  INPUT "ENTER CC/INCREMENT=";
     VI: VTAB 7: HTAB 1: PRINT "R
     ESOLUTION=";VI;" CC/LINE"
168  PRINT "AVERAGE RATE (CC/HR)=
     "
169  INPUT "PROGRAM FLOW RATE(CC/
     HR)=";DR: REM   DR=DESIRED RA
     TE
170  INPUT "DELAY START TIME (HRS
     )=";DS
171  H1 = 0:H2 = 0:H3 = 0: REM   P#
     =#PULSES IN TIME PERIOD  T#=
     LENGTH OF TIME PERIOD H#=FLO
     WRATE FOR EACH TIME PERIOD
172  INPUT "MOTOR POSITION=";M1
173  MP = M1:MT = M1: GOSUB 1500
174  POKE (RESET),0: POKE (RESET)
     ,255: POKE (RESET),254
175  LTIM = 0:TIME = 0:SEC = 0: GOSUB
     1100
178  GOTO 500
179  REM   READ BITS SUBROUTINE
180  PBITS = 255 -  PEEK (DET)
185  FOR Y = 1 TO 100: NEXT Y
190  TBITS = 255 -  PEEK (LOCTIM)
240  REM   COMPUTE AND DISPLAY TIM
     E
250  IF (TBITS - SEC) < 0 THEN LT
     IM = LTIM + 1
260 TIME = TBITS + (LTIM * 32): REM
     ONLY 5BITS
270 SEC = TBITS: REM   RESET BITS
     < 64 SECS
280 HRS =   INT (TIME / 3600):MIN =
      INT (TIME / 60) - (HRS * 60
     )
290 SC = TIME - ((MIN * 60) + (HR
     S * 3600)): REM   SC=SECONDS
     DISPLAY
300  REM   PRINT DISPLAY AB:CD:EF
310 A =   INT (HRS / 10):B = HRS -
     (A * 10)
320 C =   INT (MIN / 10):D = MIN -
     (C * 10)
330 E =   INT (SC / 10):F = SC - (
     E * 10)
331  VTAB 3: HTAB 6: PRINT A;B;":
     ";C;D;":";E;F
340  RETURN
```

```
380  REM   COMPUTE INCREMENTAL DIS
      TANCE
390  IF (PBITS - DCNT) < 0 THEN Q
     IN = QIN + 1
400 DIST = PBITS + (QIN * 256)
410 DCNT = PBITS
420  RETURN
500  GOSUB 179
510  GOSUB 380
580  VTAB 4: HTAB 22: PRINT DIST
590  FOR Z = 1 TO 100: NEXT Z
591  GOSUB 700
592  GOSUB 1200
600  GOTO 500
700  REM   RECORD TIME OF LAST PUL
      SE
710 DD = DIST - LDIST
720  IF DD > 0 THEN  GOSUB 800
721  IF ( ABS ((H1 + H2 + H3) / 3
     - DR)) > (DR * .05) THEN  GOSUB
     900
730  VTAB 5: HTAB 31: PRINT DT;"
      SECS"
740  VTAB 6: HTAB 28: PRINT A1;B1
     ;":";C1;D1;":";E1;F1
750  RETURN
799  REM   COMPUTE TIME SINCE LAST
      PULSE
800 DT = TIME - LPTIM
801  REM   COMPUTE ELAPSED TIMES A
     ND FLOW RATE AVGS
802 T3 = T2:T2 = T1:T1 = DT:P3 =
    P2:P2 = P1:P1 = DD
805 RA = ((P1 + P2 + P3) * VI) /
    (T1 + T2 + T3)
806 HR = ( INT (RA * 36000) / 10)

807  VTAB 8: HTAB 26: IF DIST > 3
      THEN  PRINT "            "
808  VTAB 8: HTAB 26: IF DIST > 3
      THEN  PRINT HR
810 A1 = A:B1 = B:C1 = C:D1 = D:E
    1 = E:F1 = F
811 H3 = H2:H2 = H1:H1 = HR
820 LPTIM = TIME
830 LDIST = DIST
840  RETURN
900  REM   RATE TRIGGERED MOTOR AD
     JUSTMENT
901  IF DD = 0 THEN  RETURN
902  IF DIST < 4 THEN  RETURN
903  IF (DD * VI * 3600 / DT) = (
     DR) THEN  RETURN
905  IF (DD * VI * 3600 / DT) > (
     DR) THEN  GOTO 960
907  IF (DD * VI * 3600 / DT) < (
     DR) THEN YDIR% = 0
910 RC =  ABS (TIME - LPTIME)
920 MP =  INT ( ABS (RC - IS))
```

```
921  IF MP > 10 THEN MP = 10
922  IF ((HR) = > .9 * DR) AND (
     (HR) = < 1.1 * DR) THEN MP =
     2
926  IF MT < 2 OR MT > 365 THEN M
     P = 0
928  IF  INT (RC) =  INT (IS) THEN
      MP = 0
930 MT = MP + M1: REM  TOTAL MOTO
    R STEPS
935  IF MT > 540 THEN MP = (540 -
     M1)
936  IF MT > 540 THEN MT = 540
940 M1 = MT: REM  LAST MT
940 M1 = MT: REM  LAST MT
950  GOTO 1000
960 YDIR% = 1
970 RC =  ABS (TIME - LPTIME)
980 MP =  INT ( ABS (RC - IS))
982  IF (( ABS (RC - IS)) = > .9
     * DR) AND (( ABS (RC - IS))
     = < 1.1 * DR) THEN MP = 4
986  IF MT < 2 OR MT > 365 THEN M
     P = 0
988  IF  INT (RC) =  INT (IS) THEN
      MP = 0
990 MT = M1 - MP
995  IF MT < = 0 THEN MP = M1
996  IF MT < = 0 THEN MT = 0
997 M1 = MT
1000  GOSUB 1100
1001  RETURN
1100  REM  MOTOR DRIVER
1101  VTAB 11: HTAB 1
1102  IF YDIR% = 0 THEN  PRINT "O
      PENING VALVE ";MP: VTAB 11: HTAB
      19: PRINT "STEPS"
1103  IF YDIR% = 1 THEN  PRINT "C
      LOSING VALVE ";MP: VTAB 11: HTAB
      19: PRINT "STEPS"
1104 MP =  INT (MP)
1105  IF MP = < 0 THEN  GOTO 113
      0
1110  & MOTB,MP,YDIR%,YMODE%
1120  IF  PEEK (35393) = 1 THEN  GOTO
      1120
1130  VTAB 11: HTAB 1: PRINT "

": VTAB 11: HTAB 1: PRINT
      "VALVE AT STEP NO.=";MT
1131 EU = MP + EU: VTAB 20: HTAB
     1: PRINT "MOTOR REVOLUTIONS
     =";( INT (EU / 360 * 1000) /
     1000)
1133  IF MT > 370 THEN  STOP
1134  IF MT < 0 THEN  STOP
1140  RETURN
```

```
1200 IS = (VI / DR) * 3600: REM
     NO. OF SECS/INC
1201  IF DT = 0 THEN  RETURN
1210  IF (TIME - LPTIME) < 3 THEN
      RETURN
1211  IF (TIME - LPTIME) > (1.2 *
     IS) THEN  GOSUB 1300
1220 I1 = (P1 * VI) / T1
1230  IF DD > 0 THEN IV = IV + I1

1240  VTAB 14: HTAB 1: PRINT "VOL
     . INFUSED (CC)=";( INT (100 *
     DIST * VI)) / 100
1249 EF = DIST * VI / TIME * 3600

1250  VTAB 16: HTAB 1: PRINT "EFF
     ECTIVE FLOW RATE (CC/HR)=
             ": VTAB 16: HTAB 1: PRINT
     "EFFECTIVE FLOW RATE (CC/HR)
     =";( INT (EF * 100)) / 100
1255 VE =  INT (100 * (EF - DR) *
     TIME / 3600) / 100
1260  VTAB 19: HTAB 1: PRINT "VOL
     UMETRIC ERROR (CC)=
             ": VTAB 19: HTAB 1: PRINT
     "VOLUMETRIC ERROR (CC)=";VE
1270  IF  ABS (VE) > .3 THEN  GOSUB
     1400
1299  RETURN
1300  REM   TIME TRIGGER ADJUSTMEN
     T
1305  IF MT > 360 THEN  RETURN
1310 YDIR% = 0:MP = 2
1313  IF MT > 365 THEN MP = 0
1315 MT = MP + M1:M1 = MT
1320  GOSUB 1100
1330  RETURN
1400  REM   VOL TRIGGERED ADJUST
1405  IF MT < 2 OR MT > 365 THEN
      RETURN
1420  IF VE < 0 THEN YDIR% = 0
1430  IF VE > 0 THEN YDIR% = 1
1440 MP = 2
1441  IF YDIR% = 0 THEN MT = M1 +
     MP
1442  IF YDIR% = 1 THEN MT = M1 -
     MP
1445 M1 = MT
1450  GOSUB 1100
1460  RETURN
1500  REM   DELAYED START SUBROUTI
     NE
1501  FOR V = 1 TO 500: NEXT V
1510  GOSUB 185: REM   CHECK TIME
1515  IF F = 1 THEN  GOTO 1550
1532 SD = DS * 3600: REM   SD=STAR
     T DELAY IN SEC
```

```
1540 F = 1: REM   FLAG
1550  IF TIME < SD THEN  GOTO 150
      1
1560  RETURN

]LOAD TEST1VE.3
]LIST

1 DET = 49316
2 POWR = 49312
3 RESET = 49314
4 LOCTIM = 49318
5  REM   INITIALIZE
10  POKE (POWR + 1),0
20  POKE (POWR),255
30  POKE (POWR + 1),4
40  POKE (POWR),255
50  POKE (RESET + 1),0
60  POKE (RESET),255
70  POKE (RESET + 1),4
80  POKE (RESET),253
90  POKE (DET + 1),0
100  POKE (DET),0
110  POKE (DET + 1),4
111  POKE (DET),255
120  POKE (LOCTIM + 1),0
130  POKE (LOCTIM),0
140  POKE (LOCTIM + 1),4
141  POKE (LOCTIME),255
142 RA = 0:HR = 0: REM   RA=AVG RA
    TE CC/SEC   HR=AVR RATE CC/H
    R
143 DD = 0:DT = 0:DIST = 0:TIME =
     0
144 LPTIM = 0:LTIM = 0:LDIST = 0
145  REM   DD=DELTA DIST   DT=DELTA
      TIME   LPTIM=LAST PULSE TIM
    E   LTIM=TIMER LOOP COUNTER
    LDIST=LAST DISTANCE
146 PBITS = 0:TBITS = 0:SEC = 0
147 DCNT = 0: REM   DETECTOR COUNT

148 QIN = 0:T1 = 0:T2 = 0:T3 = 0:
    P1 = 0:P2 = 0:P3 = 0
150  REM   END INITIALIZATION CYCL
     E
151  PRINT   CHR$ (4)"BLOAD RMPDAT
     A"
152  PRINT   CHR$ (4)"BLOAD RMPDAT
     B"
153  PRINT   CHR$ (4)"BRUN AMPRAMP
     "
154  CALL 36864:YMODE% = 0
155  POKE (POWR),0
160  POKE (RESET),254: REM   RESET
     S BOTH COUNTERS
161  HOME : HTAB 9: PRINT "I-FLOW
      CORPORATION"
```

```
162  HTAB 9: PRINT "CONTROL VALVE
     DEMO"
163  PRINT "TIME="
164  PRINT "INCREMENTS TRAVELED="
165  PRINT "TIME BETWEEN LAST TWO
     PULSES="
166  PRINT "ACTUAL TIME OF LAST P
     ULSE="
167  INPUT "ENTER CC/INCREMENT=";
     VI: VTAB 7: HTAB 1: PRINT "R
     ESOLUTION=";VI;" CC/LINE"
168  PRINT "AVERAGE RATE (CC/HR)=
     "
169  INPUT "PROGRAM    RATE(CC/
     HR)=";DR: REM     DR DES,RGD RATE
170  GOSUB 1200: REM  COMPUTE TIM
     E CONSTANTS AND CORRECTION
171  H1 = 0:H2 = 0:H3 = 0: REM  P#
     =#PULSES IN TIME PERIOD   T#=
     LENGTH OF TIME PERIOD H#=FLO
     WRATE FOR EACH TIME PERIOD
172  INPUT "MOTOR POSITION";M1: VTAB
     10: HTAB 1: PRINT "
                          "
173  MP = M1:MT = M1: GOSUB 1100
174  POKE (RESET),0: POKE (RESET)
     ,255: POKE (RESET),254
178  GOTO 500
179  REM  READ BITS SUBROUTINE
180  PBITS = 255 -  PEEK (DET)
185  FOR Y = 1 TO 100: NEXT Y
190  TBITS = 255 -  PEEK (LOCTIM)
240  REM  COMPUTE AND DISPLAY TIM
     E
250  IF (TBITS - SEC) < 0 THEN LT
     IM = LTIM + 1
260  TIME = TBITS + (LTIM * 32): REM
     ONLY 5BITS
270  SEC = TBITS: REM  RESET BITS
     < 64 SECS
280  HRS =   INT (TIME / 3600):MIN =
      INT (TIME / 60) - (HRS * 60
     )
290  SC = TIME - ((MIN * 60) + (HR
     S * 3600)): REM  SC=SECONDS
     DISPLAY
300  REM  PRINT DISPLAY AB:CD:EF
310  A =   INT (HRS / 10):B = HRS -
     (A * 10)
320  C =   INT (MIN / 10):D = MIN -
     (C * 10)
330  E =   INT (SC / 10):F = SC - (
     E * 10)
331  VTAB 3: HTAB 6: PRINT A;B;":
     ";C;D;":";E;F
340  RETURN
```

```
380  REM   COMPUTE INCREMENTAL DIS
      TANCE
390  IF (PBITS - DCNT) < 0 THEN Q
     IN = QIN + 1
400  DIST = PBITS + (QIN * 256)
410  DCNT = PBITS
420  RETURN
500  GOSUB 179
510  GOSUB 380
580  VTAB 4: HTAB 22: PRINT DIST
590  FOR Z = 1 TO 100: NEXT Z
591  GOSUB 700
592  GOSUB 1200
600  GOTO 500
700  REM   RECORD TIME OF LAST PUL
      SE
710  DD = DIST - LDIST
720  IF DD > 0 THEN  GOSUB 800
721  IF ( ABS ((H1 + H2 + H3) / 3
      - DR)) > (DR * .05) THEN  GOSUB
      900
730  VTAB 5: HTAB 31: PRINT DT;"
      SECS"
740  VTAB 6: HTAB 28: PRINT A1;B1
     ;":";C1;D1;":";E1;F1
750  RETURN
799  REM   COMPUTE TIME SINCE LAST
      PULSE
800  DT = TIME - LPTIM
801  REM   COMPUTE ELAPSED TIMES A
      ND FLOW RATE AVGS
802  T3 = T2:T2 = T1:T1 = DT:P3 =
     P2:P2 = P1:P1 = DD
805  RA = ((P1 + P2 + P3) * VI) /
      (T1 + T2 + T3)
806  HR = ( INT (RA * 36000) / 10)

807  VTAB 8: HTAB 26: IF DIST > 3
      THEN  PRINT "          "
808  VTAB 8: HTAB 26: IF DIST > 3
      THEN  PRINT HR
810  A1 = A:B1 = B:C1 = C:D1 = D:E
     1 = E:F1 = F
811  H3 = H2:H2 = H1:H1 = HR
820  LPTIM = TIME
830  LDIST = DIST
840  RETURN
900  REM   RATE TRIGGERED MOTOR AD
      JUSTMENT
901  IF DD = 0 THEN  RETURN
902  IF DIST < 4 THEN  RETURN
903  IF (DD * VI * 3600 / DT) = (
     DR) THEN  RETURN
905  IF (DD * VI * 3600 / DT) > (
     DR) THEN  GOTO 960
907  IF (DD * VI * 3600 / DT) < (
     DR) THEN YDIR% = 0
```

```
910 RC = ABS (TIME - LPTIME)
920 MP = INT ( ABS (RC - IS))
921  IF MP > 10 THEN MP = 10
922  IF ((HR) = > .9 * DR) AND (
     (HR) = < 1.1 * DR) THEN MP =
     2
928  IF INT (RC) = INT (IS) THEN
     MP = 0
930 MT = MP + M1: REM  TOTAL MOTO
    R STEPS
935  IF MT > 540 THEN MP = (540 -
     M1)
936  IF MT > 540 THEN MT = 540
940 M1 = MT: REM  LAST MT
950  GOTO 1000
960 YDIR% = 1
970 RC = ABS (TIME - LPTIME)
980 MP = INT ( ABS (RC - IS))
981  IF MP > 10 THEN MP = 10
982  IF ((HR) = > .9 * DR) AND (
     (HR) = < 1.1 * DR) THEN MP =
     4
988  IF INT (RC) = INT (IS) THEN
     MP = 0
990 MT = M1 - MP
995  IF MT < = 0 THEN MP = M1
996  IF MT < = 0 THEN MT = 0
997 M1 = MT
1000  GOSUB 1100
1001  RETURN
1100  REM  MOTOR DRIVER
1101  VTAB 11: HTAB 1
1102  IF YDIR% = 0 THEN  PRINT "O
     PENING VALVE ";MP: VTAB 11: HTAB
     19: PRINT "STEPS"
1103  IF YDIR% = 1 THEN  PRINT "C
     LOSING VALVE ";MP: VTAB 11: HTAB
     19: PRINT "STEPS"
1104 MP = INT (MP)
1105  IF MP = < 0 THEN  GOTO 113
     0
1110  & MOTB,MP,YDIR%,YMODE%
1120  IF  PEEK (35393) = 1 THEN  GOTO
     1120
1130  VTAB 11: HTAB 1: PRINT "
     ": VTAB 11: HTAB 1: PRINT
     "VALVE AT STEP NO.=";MT
1133  IF MT > 365 THEN  STOP
1134  IF MT < 2 THEN  STOP
1140  RETURN
1200 IS = (VI / DR) * 3600: REM
    NO. OF SECS/INC
1201  IF DT = 0 THEN  RETURN
1210  IF (TIME - LPTIME) < 3 THEN
     RETURN
1211  IF (TIME - LPTIME) > (1.2 *
     IS) THEN  GOSUB 1300
```

```
1220 I1 = (P1 * VI) / T1
1230 IF DD > 0 THEN IV = IV + I1

1240 VTAB 14: HTAB 1: PRINT "VOL
     . INFUSED (CC)=";( INT (100 *
     DIST * VI)) / 100
1249 EF = DIST * VI / TIME * 3600

1250 VTAB 16: HTAB 1: PRINT "EFF
     ECTIVE FLOW RATE (CC/HR)=
              ": VTAB 16: HTAB 1: PRINT
     "EFFECTIVE FLOW RATE (CC/HR)
     =";( INT (EF * 100)) / 100
1255 VE = INT (100 * (EF - DR) *
     TIME / 3600) / 100
1260 VTAB 19: HTAB 1: PRINT "VOL
     UMETRIC ERROR (CC)=
              ": VTAB 19: HTAB 1: PRINT
     "VOLUMETRIC ERROR (CC)=";VE
1270 IF ABS (VE) > .3 THEN GOSUB
     1400
1299 RETURN
1300 REM   TIME TRIGGER ADJUSTMENT
1305 IF MT > 360 THEN RETURN
1310 YDIR% = 0:MP = 1:MT = MP + M
     1:M1 = MT
1320 GOSUB 1100
1330 RETURN
1400 REM   VOL TRIGGERED ADJUST
1405 IF MT > 360 THEN RETURN
1420 IF VE < 0 THEN YDIR% = 0
1430 IF VE > 0 THEN YDIR% = 1
1440 MP = 1
1441 IF YDIR% = 0 THEN MT = M1 +
     MP
1442 IF YDIR% = 1 THEN MT = M1 -
     MP
1445 M1 = MT
1450 GOSUB 1100
1460 RETURN

]LOAD DEMO1
]LIST

1  DET = 49316
2  POWR = 49312
3  RESET = 49314
4  LOCTIM = 49318
5  REM   INITIALIZE
10  POKE (POWR + 1),0
20  POKE (POWR),255
30  POKE (POWR + 1),4
40  POKE (POWR),255
50  POKE (RESET + 1),0
60  POKE (RESET),255
70  POKE (RESET + 1),4
80  POKE (RESET),253
90  POKE (DET + 1),0
```

```
100  POKE (DET),0
110  POKE (DET + 1),4
111  POKE (DET),255
120  POKE (LOCTIM + 1),0
130  POKE (LOCTIM),0
140  POKE (LOCTIM + 1),4
141  POKE (LOCTIME),255
142  RA = 0:HR = 0: REM   RA=AVG RATE CC/SEC   HR=AVR RATE CC/HR
143  DD = 0:DT = 0:DIST = 0:TIME = 0
144  LPTIM = 0:LTIM = 0:LDIST = 0
145  REM   DD=DELTA DIST   DT=DELTA TIME   LPTIM=LAST PULSE TIME   LTIM=TIMER LOOP COUNTER   LDIST=LAST DISTANCE
146  PBITS = 0:TBITS = 0:SEC = 0
147  DCNT = 0: REM   DETECTOR COUNT
148  QIN = 0:T1 = 0:T2 = 0:T3 = 0:P1 = 0:P2 = 0:P3 = 0
150  REM   END INITIALIZATION CYCLE
151  PRINT  CHR$ (4)"BLOAD RMPDATA"
152  PRINT  CHR$ (4)"BLOAD RMPDATB"
153  PRINT  CHR$ (4)"BRUN AMPRAMP"
154  CALL 36864:YMODE% = 0
155  POKE (POWR),0
160  POKE (RESET),254: REM   RESETS BOTH COUNTERS
161  HOME : HTAB 9: PRINT "I-FLOW CORPORATION"
162  HTAB 9: PRINT "CONTROL VALVE DEMO"
163  PRINT "TIME="
164  PRINT "INCREMENTS TRAVELED="
165  PRINT "TIME BETWEEN LAST TWO PULSES="
166  PRINT "ACTUAL TIME OF LAST PULSE="
167  INPUT "ENTER CC/INCREMENT=";VI: VTAB 7: HTAB 1: PRINT "RESOLUTION=";VI;" CC/LINE"
168  PRINT "AVERAGE RATE (CC/HR)="
169  INPUT "PROGRAM FLOW RATE(CC/HR)=";DR: REM   DR=DESIRED RATE
170  GOSUB 1200: REM   COMPUTE TIME CONSTANTS AND CORRECTION
171  H1 = 0:H2 = 0:H3 = 0: REM   P#=#PULSES IN TIME PERIOD  T#=LENGTH OF TIME PERIOD  H#=FLO
```

```
     WRATE FOR EACH TIME PERIOD
172  INPUT "MOTOR POSITION";M1: VTAB
     10: HTAB 1: PRINT "
                       "
173  MP = M1:MT = M1: GOSUB 1100
174  POKE (RESET),0: POKE (RESET)
     ,255: POKE (RESET),254
178  GOTO 500
179  REM  READ BITS SUBROUTINE
180  PBITS = 255 - PEEK (DET)
185  FOR Y = 1 TO 100: NEXT Y
190  TBITS = 255 - PEEK (LOCTIM)
240  REM  COMPUTE AND DISPLAY TIM
     E
250  IF (TBITS - SEC) < 0 THEN LT
     IM = LTIM + 1
260  TIME = TBITS + (LTIM * 32): REM
       ONLY 5BITS
270  SEC = TBITS: REM  RESET BITS
      < 64 SECS
280  HRS =  INT (TIME / 3600):MIN =
      INT (TIME / 60) - (HRS * 60
     )
290  SC = TIME - ((MIN * 60) + (HR
     S * 3600)): REM  SC=SECONDS
     DISPLAY
300  REM  PRINT DISPLAY AB:CD:EF
310  A =  INT (HRS / 10):B = HRS -
      (A * 10)
320  C =  INT (MIN / 10):D = MIN -
      (C * 10)
330  E =  INT (SC / 10):F = SC - (
     E * 10)
331  VTAB 3: HTAB 6: PRINT A;B;":
     ";C;D;":";E;F
340  RETURN
380  REM  COMPUTE INCREMENTAL DIS
     TANCE
390  IF (PBITS - DCNT) < 0 THEN Q
     IN = QIN + 1
400  DIST = PBITS + (QIN * 256)
410  DCNT = PBITS
420  RETURN
500  GOSUB 179
510  GOSUB 380
580  VTAB 4: HTAB 22: PRINT DIST
590  FOR Z = 1 TO 100: NEXT Z
591  GOSUB 700
592  GOSUB 1200
600  GOTO 500
700  REM  RECORD TIME OF LAST PUL
     SE
710  DD = DIST - LDIST
720  IF DD > 0 THEN  GOSUB 800
721  IF ( ABS ((H1 + H2 + H3) / 3
      - DR)) > (DR * .05) THEN  GOSUB
```

```
            900
730   VTAB 5: HTAB 31: PRINT DT;"
       SECS"
740   VTAB 6: HTAB 28: PRINT A1;B1
       ;":";C1;D1;":";E1;F1
750   RETURN
799   REM   COMPUTE TIME SINCE LAST
       PULSE
800 DT = TIME - LPTIM
801   REM   COMPUTE ELAPSED TIMES A
       ND FLOW RATE AVGS
802 T3 = T2:T2 = T1:T1 = DT:P3 =
     P2:P2 = P1:P1 = DD
805 RA = ((P1 + P2 + P3) * VI) /
     (T1 + T2 + T3)
806 HR = ( INT (RA * 36000) / 10)

807   VTAB 8: HTAB 26: IF DIST > 3
       THEN  PRINT "           "
808   VTAB 8: HTAB 26: IF DIST > 3
       THEN  PRINT HR
810 A1 = A:B1 = B:C1 = C:D1 = D:E
     1 = E:F1 = F
811 H3 = H2:H2 = H1:H1 = HR
820 LPTIM = TIME
830 LDIST = DIST
840   RETURN
900   REM   RATE TRIGGERED MOTOR AD
       JUSTMENT
901   IF DD = 0 THEN  RETURN
902   IF DIST < 4 THEN  RETURN
903   IF (DD * VI * 3600 / DT) = (
       DR) THEN  RETURN
905   IF (DD * VI * 3600 / DT) > (
       DR) THEN  GOTO 960
907   IF (DD * VI * 3600 / DT) < (
       DR) THEN  YDIR% = 0
910 RC =    ABS (TIME - LPTIME)
920 MP =    INT ( ABS (RC - IS))
921   IF MP > 25 THEN  MP = 25
922   IF((HR) = > 9 * DR) AND (
       (HR) = < 1.1 * HR) THEN  MP =
       2
928   IF  INT (RC) =  INT (IS) THEN
       MP = 0
929   IF MP > 4 THEN  MP = 4
930 MT = MP + M1: REM   TOTAL MOTO
     R STEPS
935   IF MT > 540 THEN  MP = (540 -
       M1)
936   IF MT > 540 THEN  MT = 540
940 M1 = MT: REM   LAST MT
950    GOTO 1000
960 YDIR% = 1
970 RC =  ABS (TIME - LPTIME)
980 MP =    INT ( ABS (RC - IS))
981   IF MP > 25 THEN  MP = 25
```

```
982  IF ((HR) = > .9 * DR) AND (
     (HR) = < 1.1 * HR) THEN MP =
     4
988  IF  INT (RC) =  INT (IS) THEN
     MP = 0
990 MT = M1 - MP
995  IF MT < = 0 THEN MP = M1
996  IF MT < = 0 THEN MT = 0
997 M1 = MT
1000  GOSUB 1100
1001  RETURN
1100  REM  MOTOR DRIVER
1101  VTAB 11: HTAB 1
1102  IF YDIR% = 0 THEN  PRINT "O
     PENING VALVE ";MP: VTAB 11: HTAB
     19: PRINT "STEPS"
1103  IF YDIR% = 1 THEN  PRINT "C
     LOSING VALVE ";MP: VTAB 11: HTAB
     19: PRINT "STEPS"
1104 MP =  INT (MP)
1105  IF MP = < 0 THEN  GOTO 113
     0
1110  & MOTB,MP,YDIR%,YMODE%
1120  IF  PEEK (35393) = 1 THEN  GOTO
     1120
1130  VTAB 11: HTAB 1: PRINT "

": VTAB 11: HTAB 1: PRINT
     "VALVE AT STEP NO.=";MT
1133  IF MT > 365 THEN  STOP
1134  IF MT < 2 THEN  STOP
1140  RETURN
1200 IS = (VI / DR) * 3600: REM
     NO. OF SECS/INC
1201  IF DT = 0 THEN  RETURN
1210  IF (TIME - LPTIME) < 3 THEN
     RETURN
1211  IF (TIME - LPTIME) > (1.2 *
     IS) THEN  GOSUB 1300
1220 I1 = (P1 * VI) / T1
1230  IF DD > 0 THEN  IV = IV + I1
1240  VTAB 14: HTAB 1: Print "VOL.  Infused (cc)=" ;Print (100 *
     DIST * VI)) / 100
1249 EF = DIST * VI / TIME * 3600

1250  VTAB 16: HTAB 1: PRINT "EFF
     ECTIVE FLOW RATE (CC/HR)=
          ": VTAB 16: HTAB 1: PRINT
     "EFFECTIVE FLOW RATE (CC/HR)
     =";( INT (EF * 100)) / 100
1255 VE =  INT (100 * (EF - DR) *
     TIME / 3600) / 100
1260  VTAB 19: HTAB 1: PRINT "VOL
     UMETRIC ERROR (CC)=
          ": VTAB 19: HTAB 1: PRINT
     "VOLUMETRIC ERROR (CC)=";VE
1270  IF  ABS (VE) > .5 THEN  GOSUB
```

```
1299  RETURN      1400
1300  REM    TIME TRIGGER ADJUSTMENT
1305   IF MT > 360 THEN  RETURN
1310  YDIR% = 0:MP = 1:MT = MP + M1:M1 = MT
1320   GOSUB 1100
1330  RETURN
1400  REM   VOL TRIGGERED ADJUST
1405   IF MT > 360 THEN  RETURN
1420   IF VE < 0 THEN YDIR% = 0
1430   IF VE > 0 THEN YDIR% = 1
1440  MP = 1
1441   IF YDIR% = 0 THEN MT = M1 + MP
1442   IF YDIR% = 1 THEN MT = M1 - MP
1445  M1 = MT
1450   GOSUB 1100
1460   RETURN
```

I claim:

1. A multiple fluid cartridge assembly comprising:
    a housing;
    a plurality of flexible compartments for containing fluids, each compartment having an outlet through which said fluids are expelled;
    a pressure roller movable within said housing to compress said plurality of flexible compartments, said pressure roller including engagement means extending from said housing;
    a plurality of access tubes, each tube connected to the outlet of one of said compartment;
    a multiple port connector, each port being connected to one of said access tubes; and
    flow restrictor means for adjustably compressing said plurality of access tubes to regulate the flow of fluid therethrough, said flow restrictor means including:
    a compression member for contacting and pressing against said access tubes;
    a spring located adjacent said compression member so that said spring may exert force against said compression member;
    a rotatable threaded cylindrical member; and
    a non-rotating member having a threaded hole engaged by said cylindrical member, said non-rotating member being adjacent said spring opposite said compression member so that rotation of said cylindrical member adjusts the force exerted by said non-rotating member on said spring and consequently adjusting the force exerted by said spring on said compression member.

2. The multiple fluid cartridge of claim 1 further comprising gear means extending from said housing and connected to said flow restrictor means for adjusting the pressure exerted by said flow restrictor means on said plurality of access tubes.

3. The multiple fluid cartridge of claim 1 further comprising a strip having position indicating markings along its length, said strip being arranged on said housing with its length in the direction of movement of said pressure roller.

4. The multiple cartridge of claim 1 further comprising a resilient base within said housing beneath said plurality of compartments and means for holding said roller against said base to prevent fluid from leaking within any of said compartments between said roller and said base.

5. The multiple cartridge of claim 4 wherein said means for holding said roller comprises a pair of slots in opposite sides of said housing.

6. A fluid dispensing cartridge assembly comprising:
    a housing;
    at least one flexible compartment for containing fluid, each compartment being connected by an access tube to an outlet for expelling fluid;
    a pressure roller movable within said housing to compress said at least one flexible compartment, said pressure roller including means extending from said housing for engagement with a drive mechanism;
    position indicating markings arranged along the length of said housing in the direction of movement of said pressure roller; and
    flow restrictor means for adjustably compressing each said access tube to regulate the flow of fluid therethrough, said flow restrictor means including:
    a compression member for contacting and pressing against each said access tube;
    a spring located adjacent said compression member so that said spring may exert force against said compression member;
    a rotatable threaded cylindrical member; and
    a non-rotating member having a threaded hole engaged by said cylindrical member, said non-rotating member being adjacent said spring opposite said compression member so the rotation of said cylindrical member adjusts the force exerted by said non-rotating member on said spring and consequently adjusting the force exerted by said spring on said compression member.

7. The fluid dispensing cartridge of claim 6 wherein said position indicating markings are provided on a reflective strip on said housing.

8. The fluid dispensing cartridge of claim 6 further comprising gear means extending from said housing and connected to said flow restrictor means to control the adjustment of the pressure exerted by said flow restrictor means on said plurality of access tubes.

9. The fluid dispensing cartridge of claim 6 further comprising a resilient base within said housing beneath said at least one compartment and means for holding said roller against said base to prevent fluid from leaking within any of said compartments between said roller and said base.

10. The fluid dispensing cartridge of claim 9 wherein said means for holding said roller comprises a pair of slots in opposite sides of said housing.

11. A fluid dispensing cartridge assembly comprising:
a housing having a resilient base;
at least one flexible compartment formed on said resilient base for containing fluid, each compartment being connected by an access tube to an outlet for expelling fluid;
a roller for compressing said at least one compartment against said resilient base to squeeze fluid out through the outlets of said at least one compartment;
means for holding said roller against said base to prevent fluid from leaking within any of said at least one compartments between said roller and said base; and
flow restrictor means for adjustably compressing each said access tube to regulate the flow of fluid therethrough, said flow restrictor means including:
a compression member for contacting and pressing against each said access tube;
a spring located adjacent said compression member so that said spring may exert force against said compression member;
a rotatable threaded cylindrical member; and
a non-rotating member having a threaded hole engaged by said cylindrical member, said non-rotating member being adjacent said spring opposite said compression member so that rotation of said cylindrical member adjusts the force exerted by said non-rotating member on said spring and consequently adjusting the force exerted by said spring on said compression member.

12. The fluid dispensing cartridge of claim 11 wherein said means for holding said roller comprises a pair of slots in opposite sides of said housing.

13. The fluid dispensing cartridge of claim 11 further comprising gear means extending from said housing and connected to said flow restrictor means to control the adjustment of the pressure exerted by said flow restrictor means on said plurality of access tubes.

14. The fluid dispensing cartridge of claim 11 further comprising a strip having position indicating markings along its length, said strip being arranged on said housing with its length in the direction of movement of said pressure roller.

15. A programmable pump comprising:
a housing;
a sliding member within said housing;
means for applying a substantially constant force to said slidable member;
means for detecting the position of said slidable member within said housing;
a motor;
means, coupled to said motor, for regulating a flow restrictor; and
programmable controller means responsive to said position detecting means for operating said motor to regulate the flow restrictor such that said slidable member moves through said housing to provide a preprogrammed volume of flow per the time duration of the infusion.

16. The programmable pump of claim 15 wherein said position detecting means comprises an optical emitter and detector carried by said slidable member.

17. The programmable pump of claim 16 wherein said position detecting means further comprises a strip having position indicating markings along its length, said strip being arranged in said housing with its length in the direction of movement of said slidable member and said optical emitter and detector interact with said strip to read the markings thereon as said slidable member moves relative thereto.

18. The programmable pump of claim 15 wherein said means for applying a substantially constant force comprises a constant force spring.

19. The programmable pump of claim 18 wherein said constant force spring comprises a coil prevented from translational movement within said housing having one end connected to said slidable member.

20. An infusion pump comprising:
a pump housing for receiving at least one fluid containing compartment;
a constant force spring having a free end at the exterior of a coil, said coil mounted within said housing so as to be prevented from translational movement;
means for applying pressure coupled to the free end of said constant force spring such that said pressure applying means is pulled against said at least one compartment for pushing fluid therefrom; and
flow restrictor means for regulating the flow of fluid out of said at least one compartment;
a motor on said pump housing; and
gear means connected to said motor for adjusting said flow restrictor means.

21. The infusion pump of claim 20 wherein said pressure applying means comprises a slidable member connected to the free end of said constant force spring and a roller engaged by said slidable member so that said roller is pulled against said at least one compartment for squeezing fluid therefrom.

22. The infusion pump of claim 21 wherein said fluid containing compartment is a flexible compartment formed on a resilient base and said roller is held against said base to prevent fluid from leaking within said compartment between said roller and said resilient base.

23. The infusion pump of claim 20 further comprising:
a strip having position indicating markings along its length, said strip being arranged with its length in the direction of movement of said pressure applying means; and
an optical emitter and detector carried by said pressure applying means to read the position of said pressure applying means relative to said at least one compartment as said pressure applying means is pulled against said at least one compartment.

24. The infusion pump of claim 23 further comprising programmable controller means responsive to said emitter and detector for controlling said motor to set said flow restrictor means so that fluid is pushed from said at least one compartment at a predetermined rate.

25. The infusion pump of claim 21 wherein said at least one fluid containing compartment is located on a cartridge insertable into said pump housing.

26. An infusion pump comprising:
a pump housing for receiving at least one fluid containing compartment located on a cartridge insertable into said pump housing;

a constant force spring having a free end at the exterior of a coil, said coil mounted within said housing so as to be prevented from translational movement;

a slidable member connected to the free end of said constant force spring; and a roller engaged by said slidable member so that said roller is pulled against said at least one compartment for squeezing fluid therefrom, wherein said roller includes an engagement means extending through slots of said cartridge for engaging said slidable member such that when said cartridge is loaded into said pump housing said engagement means engages said slidable member to unwind said constant force spring.

27. A programmable infusion pump comprising:
a pump housing for receiving a cartridge housing, said cartridge housing containing at least one flexible fluid containing compartment each compartment having an access tube through which fluid can be expelled;

a substantially constant force spring having a free end on the exterior of a coil, said coil mounted within said pump housing so as to be prevented from translational movement;

a slidable member connected to the free end of said spring;

a roller carried in said cartridge housing and engaged by said slidable member for compressing said at least one compartment to squeeze fluid out through the access tubes of said at least one compartment;

flow restrictor means for restricting the flow of fluid out through the access tubes;

a motor coupled to said flow restrictor means for regulating said flow restrictor means;

means for detecting the position of said roller; and programmable controller means responsive to said position detecting means for operating said motor to regulate the flow restrictor such that as said roller is pulled through said cartridge housing by said slidable member, a preprogrammed volume of fluid flows out of said at least one flexible compartment per time duration of the infusion.

28. The programmable infusion pump of claim 27 further comprising a strip having position indicating markings along its length, said strip being arranged on said cartridge housing with its length in the direction of movement of said roller.

29. The programmable infusion pump of claim 28 wherein said position detecting means comprises an optical emitter and detector carried by said slidable member to read the position of said slidable member relative to said at least one compartment as said roller is pulled across said at least one compartment, the position of said slidable member being directly related to the position of said pressure roller.

30. The programmable infusion pump of claim 27 wherein said flow restrictor means includes:
a compression member for contacting and pressing against said access tubes;

a spring located adjacent said compression member so that said spring may exert force against said compression member;

a rotatable threaded cylindrical member; and a non-rotating member having a threaded hold engaged by said cylindrical member, said non-rotating member being adjacent said spring opposite said compression member so that rotation of said cylindrical member adjusts the force exerted by said non-rotating member on said spring and consequently adjusting the force exerted by said spring on said compression member.

31. The programmable infusion pump of claim 27 further comprising a multiple port connector, each port being connected to one of said access tubes.

32. The programmable infusion pump of claim 27 wherein said cartridge housing further comprises a resilient base within said housing beneath said at least one compartment and means for holding said roller against said base to prevent fluid from leaking within any of said compartments between said roller and said base.

33. A method for maintaining a predetermined infusion rate comprising the steps of:
providing infusion apparatus having a fluid containing compartment and a movable member for pushing fluid out of said compartment;

counting the amount of time for which said infusion apparatus is being used during the infusion;

determining the time it takes said movable member to move from a first position to a second position;

determining the volume of fluid infused between the first position and the second position;

dividing the volume of fluid infused between the first position and the second position by the amount of time it took to move from the first position to the second position to determine the current infusion rate;

comparing the current infusion rate with the predetermined infusion rate; and adjusting the rate of fluid flow from said infusion apparatus by adjusting a flow restrictor means to vary the size of an outlet from said compartment when said current infusion rate differs from said predetermined infusion rate by more than a predetermined tolerance.

34. The method of claim 33 further comprising locating the position of said movable member by emitting a ray of light at a strip of position indicating markings, receiving any light reflected from said position indicating markings and interpreting the received light to determine the position of said movable member.

35. A method of infusing a predetermined volume of fluid over a predetermined infusion time period comprising the steps of:
providing infusion apparatus having a fluid containing compartment and a means for expelling fluid from said compartment;

counting the time as said infusion apparatus is used during an infusion;

determining the time it takes to infuse a sample volume of fluid, said sample volume being smaller than said predetermined volume;

dividing the sample volume by the amount of time it took to infuse said sample volume to determine the current infusion rate;

determining a rate error as a function of the current infusion rate and a desired rate which will result in the infusion of the predetermined volume of fluid at the end of the predetermined infusion time period;

determining the total volume of fluid infused between the start of the infusion and the end of the infusion of said sample volume;

determining a volumetric error as a function of the total volume of fluid infused and a desired volume which is the product of the predetermined volume of fluid and the rate of the time elapsed between the start of infusion and the end of the infusion of said sample volume to the predetermined infusion time period; and adjusting the flow of fluid from said infusion apparatus by adjusting a flow restrictor means to vary the size of an outlet from said compartment when either said rate error exceeds a predetermined rate tolerance or said volumetric error exceeds a predetermined volume tolerance.

36. The method of claim 35 further comprising the step of detecting the position of movable member, said movable member being used to push fluid out of said compartment and wherein the volume of infused fluid is determined as a function of the position of said movable member.

37. The method of claim 36 wherein the step of detecting position comprises emitting a ray of light at a strip of position indicating markings, receiving any light reflected from said position indicating markings and interpreting the received light to determine the position of said movable member.

* * * * *